US008663658B2

(12) United States Patent
Park et al.

(10) Patent No.: US 8,663,658 B2
(45) Date of Patent: Mar. 4, 2014

(54) REVAPRAZAN-CONTAINING SOLID DISPERSION AND PROCESS FOR THE PREPARATION THEREOF

(75) Inventors: Young-Joon Park, Gwacheon (KR); Chang-Keun Hyun, Suwon (KR)

(73) Assignee: Yuhan Corporation, Seoul (KR)

( * ) Notice: Subject to any disclaimer, the term of this patent is extended or adjusted under 35 U.S.C. 154(b) by 777 days.

(21) Appl. No.: 12/520,037

(22) PCT Filed: Dec. 21, 2007

(86) PCT No.: PCT/KR2007/006738
§ 371 (c)(1),
(2), (4) Date: Jun. 18, 2009

(87) PCT Pub. No.: WO2008/078922
PCT Pub. Date: Jul. 3, 2008

(65) Prior Publication Data
US 2010/0041688 A1    Feb. 18, 2010

(30) Foreign Application Priority Data
Dec. 22, 2006    (KR) ........................ 10-2006-0132722

(51) Int. Cl.
A61K 31/506    (2006.01)
A61K 47/48    (2006.01)

(52) U.S. Cl.
USPC ......................................... 424/400; 514/275

(58) Field of Classification Search
None
See application file for complete search history.

(56) References Cited

U.S. PATENT DOCUMENTS

| 6,221,395 B1 | 4/2001 | Maggi et al. |
| 2002/0150624 A1* | 10/2002 | Watanabe et al. ............. 424/487 |
| 2005/0020634 A1* | 1/2005 | Terashita et al. ............. 514/337 |
| 2006/0153913 A1 | 7/2006 | Yamane et al. |
| 2006/0204572 A1 | 9/2006 | Higuchi et al. |

FOREIGN PATENT DOCUMENTS

| CA | 2390092 A1 | 5/2001 |
| RU | 2129549 C1 | 4/1999 |
| RU | 2185820 C2 | 7/2002 |
| RU | 2288704 C2 | 12/2006 |
| WO | WO 93/16686 A1 | 9/1993 |
| WO | 96/05177 A1 | 2/1996 |
| WO | WO2007/070164 | * 10/2006 |
| WO | 2007/064128 A1 | 6/2007 |

OTHER PUBLICATIONS

Vakil. New Pharmacological Agents for use in Treatement of Gastro-Oesophageal Reflux Disease. Alimentary Pharmacology and Therapeutics. vol. 19, Issue 10. Apr. 29, 2004 (publihed online) http://onlinelibrary.wiley.com/doi/10.1111/j.1365-2036.2004.01957.x/full (online version).*
"Technology of Drug Forms," Meditsina, 1991, vol. 2, p. 156.

(Continued)

Primary Examiner — Scott Long
Assistant Examiner — Sarah Alawadi
(74) Attorney, Agent, or Firm — Sughrue Mion, PLLC (57) ABSTRACT

The present invention provides a solid dispersion in which revaprazan particles are surface-modified with a water-soluble polymer, a water-soluble saccharide, a surfactant, or a mixture thereof and a process for preparing the same. The present invention also provides a pharmaceutical composition containing the solid dispersion and a process for preparing the pharmaceutical composition.

7 Claims, 4 Drawing Sheets

(56) References Cited

OTHER PUBLICATIONS

Abu T. M. Serajuddin, "Solid Dispersion of Poorly Water-Soluble Drugs: Early Promises, Subsequent Problems, and Recent Breakthroughs," Journal of Pharmaceutical Sciences, 1999, vol. 88, No. 10, pp. 1058-1066.

Russian Patent Office, Russian Office Action issued in corresponding RU Application No. 2009128206, dated Nov. 11, 2011.

* cited by examiner

REVAPRAZAN-CONTAINING SOLID DISPERSION AND PROCESS FOR THE PREPARATION THEREOF

CROSS REFERENCE TO RELATED APPLICATIONS

This application is a National Stage of International Application No. PCT/KR2007/006738 filed Dec. 21, 2007, claiming priority based on Korean Patent Application No. 10-2006-0132722, filed Dec. 22, 2006, the contents of which are incorporated herein by reference in their entirety.

TECHNICAL FIELD

The present invention relates to a solid dispersion in which revaprazan particles are surface-modified with a water-soluble polymer, a water-soluble saccharide, a surfactant, or a mixture thereof and a process for preparing the same. The present invention also relates to a pharmaceutical composition containing the solid dispersion and a process for preparing the pharmaceutical composition.

BACKGROUND ART

Revaprazan, whose chemical name is 5,6-dimethyl-2-(4-fluorophenylamino)-4-(1-methyl-1,2,3,4-tetrahydroisoquinolin-2-yl)pyrimidine, is represented by the following Formula 1. Revaprazan may be used in a form of an acid addition salt, including e.g., HCl salt (see International Publication No. WO 1996/05177).

Formula 1

Revaprazan or its salt is reversibly bound to a $H^+/K^+$ exchange site of a proton pump ($H^+/K^+$ ATPase) existing in a gastric parietal cell so that secretion of $H^+$ into the gastric lumen is competitively inhibited. Revaprazan or its salt is also bound to a specific site of $H^+/K^+$ ATPase, thereby inhibiting transport of $H^+$ and suppressing an acid secretion to the gastric lumen, which results in increasing the intragastric pH. Unlike irreversible proton pump inhibitors, e.g., omeprazole, revaprazan or its salt is not dependent upon acid activation of a drug in a stomach or secretion status of a proton pump. Therefore, based on the mechanism different from irreversible proton pump inhibitors, such as omeprazole, revaprazan or its salt is classified into an acid pump antagonist (APA).

Meanwhile, revaprazan has very low water-solubility, i.e. less than 0.2 mg/mL, and due to such a low solubility, its dissolution in a gastrointestinal tract is low. Therefore, when revaprazan is orally administered, its absorption rate is relatively low. Revaprazan also has strong adhesion and agglutination properties, and thus, when revaprazan is formulated into a capsule or a tablet, it may be stuck to a punch or a die, thereby showing low formulation processability.

DISCLOSURE

Technical Problem

The present inventors studied to improve physicochemical properties of revaprazan, i.e. low dissolution rate and low formulation processability. As a result, it is found that, when revaprazan particles are surface-modified with a water-soluble polymer, a water-soluble saccharide, and/or a surfactant to prepare into a form of solid dispersion, the solubility and dissolution of revaprazan are notably improved, thereby showing remarkably improved bioavailability. In addition, it is found that the adhesiveness and agglutination properties of revaprazan can be improved to result in increasing its formulation processability.

Therefore, it is an object of the present invention to provide a revaprazan-containing solid dispersion.

It is another object of the present invention to provide a pharmaceutical composition which includes the revaprazan-containing solid dispersion and a pharmaceutically acceptable carrier.

It is still another object of the present invention to provide a process for preparing the revaprazan-containing solid dispersion.

It is still another object of the present invention to provide a process for preparing the pharmaceutical composition.

Technical Solution

In accordance with an aspect of the present invention, there is provided a solid dispersion in which revaprazan particles are surface-modified with a water-soluble polymer, a water-soluble saccharide, a surfactant, or a mixture thereof.

In accordance with another aspect of the present invention, there is provided a pharmaceutical composition comprising the solid dispersion and a pharmaceutically acceptable carrier.

In accordance with still another aspect of the present invention, there is provided a process for preparing the solid dispersion, the process comprising suspending revaprazan and one of a water-soluble polymer, a water-soluble saccharide, a surfactant, and a mixture thereof in water to obtain a suspension; and drying the suspension.

In accordance with still another aspect of the present invention, there is provided a process for preparing a granule, the process comprising suspending revaprazan and one of a water-soluble polymer, a water-soluble saccharide, a surfactant, and a mixture thereof in water to obtain a suspension; and spray-drying the suspension on a pharmaceutically acceptable carrier.

In accordance with still another aspect of the present invention, there is provided a process for preparing a granule, the process comprising granulating by adding a binder solution to a mixture of the solid dispersion and a pharmaceutically acceptable carrier.

In accordance with still another aspect of the present invention, there is provided a process for preparing a tablet, the process comprising compressing a mixture of the solid dispersion and a pharmaceutically acceptable carrier, or compressing a mixture of a granule obtained from the solid dispersion and a pharmaceutically acceptable carrier.

In accordance with still another aspect of the present invention, there is provided a process for preparing a capsule, the process comprising filling a capsule with a mixture of the solid dispersion and a pharmaceutically acceptable carrier, or filling a capsule with a mixture of a granule obtained from the solid dispersion and a pharmaceutically acceptable carrier.

Advantageous Effects

In accordance with the present invention, revaprazan particles are surface-modified with a water-soluble polymer, a water-soluble saccharide, and/or a surfactant to prepare into a form of solid dispersion, thereby increasing penetration and solubility properties of the drug (i.e, revaprazan), which results in increasing the solubility and/or dissolution rate of revaprazan remarkably, thereby improving its bioavailability. And also the adhesiveness and agglutination can be decreased and thus its formulation processability can be improved. Furthermore, the solid dispersion can be prepared using water as a medium, and thus, potential problems caused by using organic solvents, e.g., safety problems caused by residual solvent, can be avoided.

BEST MODE

Through the present specification, the terminology "surface-modified" refers to coating or adhering a water-soluble polymer, a water-soluble saccharide, a surfactant, or the like, on or onto revaprazan particles.

The terminology "revaprazan" refers to 5,6-dimethyl-2-(4-fluorophenylamino)-4-(1-methyl-1,2,3,4-tetrahydroisoquinolin-2-yl)pyrimidine, including its pharmaceutically acceptable salt, such as revaprazan hydrochloride, revaprazan sulfate, revaprazan nitrate, revaprazan camphor sulfonate (i.e., revaprazan camsylate), revaprazan thiocyanate, revaprazan phosphate, revaprazan carbonate, and the like. Preferably, the terminology "revaprazan" includes revaprazan hydrochloride.

In accordance with the present invention, revaprazan particles are surface-modified with a water-soluble polymer, a water-soluble saccharide, and/or a surfactant to prepare into a form of solid dispersion, thereby increasing penetration and solubility properties of the drug (i.e, revaprazan), which results in increasing the solubility and/or dissolution rate of revaprazan remarkably, thereby improving its bioavailability. And also the adhesiveness and agglutination can be decreased and thus its formulation processability can be improved. Furthermore, the solid dispersion can be prepared using water as a medium, and thus, potential problems caused by using organic solvents, e.g., safety problems caused by residual solvent, can be avoided.

The present invention provides a solid dispersion in which revaprazan particles are surface-modified with a water-soluble polymer, a water-soluble saccharide, a surfactant, or a mixture thereof.

The water-soluble polymer may be selected from the group consisting of polyvinylpyrrolidone, hydroxypropylmethyl cellulose, hydroxypropyl cellulose, polyethylene glycol, a water-soluble polyacrylic acid copolymer (for example, Eudragit E or carbomer), polyvinyl alcohol, and a mixture thereof and, preferably selected from the group consisting of polyvinylpyrrolidone, hydroxypropylmethyl cellulose, polyethylene glycol, and a mixture thereof. More preferably, the water-soluble polymer may be polyvinylpyrrolidone.

The water-soluble saccharide may be selected from the group consisting of lactose, white sugar, sucrose, mannitol, sorbitol, xylitol, trehalose, maltitol, dulcitol, inositol, dextrin, cyclodextrin (for example, α-cyclodextrin, β-cyclodextrin, γ-cyclodextrin, or hydroxypropyl β-cyclodextrin, and specifically, hydroxypropyl β-cyclodextrin), and a mixture thereof. Preferably, the water-soluble saccharide may be selected from the group consisting of lactose, mannitol, cyclodextrin, and a mixture thereof.

The surfactant may be selected from the group consisting of sorbitan ester or polyoxyethylene sorbitan fatty acid ester (for example, polysorbate 80™), sucrose fatty acid ester (Ryoto Ester L1695™), polyethylene glycol-15-hydroxystearate (for example, Solutol HS 15™), polyoxyethylene glycolated natural or hydrogenated castor oil (for example, Cremophor RH 40™, Cremophor RH 60™), polyoxyethylene-polyoxypropylene copolymer (for example, Poloxamer 407™, Poloxamer 118™), synthetic vitamin E derivative (for example, vitamin E TPGS™), polyoxyethylene alkyl ester (for example, Brij 52 ™), fatty acid microgol glyceride (for example, Gelucire 44/14™), polyglyceryl fatty acid ester (for example, Plurol Oleique™), bile acid (for example, taurocholic acid), sodium lauryl sulfate, lecithin, glyceryl fatty acid ester (for example, glyceryl monostearate), polyoxyethylene stearate, and a mixture thereof. Preferably, the surfactant may be selected from the group consisting of sorbitan ester or polyoxyethylene sorbitan fatty acid ester, sucrose fatty acid ester, polyethylene glycol-15-hydroxystearate, polyoxyethylene glycolated natural or hydrogenated castor oil, polyoxyethylene-polyoxypropylene copolymer, synthetic vitamin E derivative, fatty acid microgol glyceride, and a mixture thereof. More preferably, the surfactant may be sucrose fatty acid ester, polyoxyethylene glycolated natural or hydrogenated castor oil, polyethylene glycol-15-hydroxystearate, polyoxyethylene-polyoxypropylene copolymer, or a mixture thereof.

The solid dispersion according to the present invention can be prepared using one or a combination of a water-soluble polymer, a water-soluble saccharide, and a surfactant. For example, a solid dispersion can be prepared by surface-modifying revaprazan particles with polyvinylpyrrolidone, sucrose fatty acid ester, and polyoxyethylene glycolated natural or hydrogenated castor oil.

The amount of revaprazan incorporated as an active ingredient in the solid dispersion according to the present invention is dependent upon a unit dosage form administered to achieve a curative objective, for example, to treat an ulcer. For example, the unit dosage form may include revaprazan in the range from 10 to 600 mg, specifically, from 50 to 400 mg. Although an average particle size of revaprazan is not limited, the average particle size thereof may be about 50 µm or less.

The amount of the water-soluble polymer, water-soluble saccharide, or surfactant which is contained in the solid dispersion according to the present invention may be adjusted considering properties of a solid dispersion to be prepared. Preferably, revaprazan particles may be surface-modified with one of a water-soluble polymer, a water-soluble saccharide, a surfactant, and a mixture thereof in an amount from 5 to 900 parts by weight, preferably from 20 to 200 parts by weight, based on 100 parts by weight of revaprazan. More preferably, revaprazan particles are surface-modified with 5 to 30 parts by weight of polyvinylpyrrolidone, 20 to 100 parts by weight of sucrose fatty acid ester, and 10 to 100 parts by weight of polyoxyethylene glycolated natural or hydrogenated castor oil, based on 100 parts by weight of revaprazan The present invention includes, within its scope, a pharmaceutical composition comprising the solid dispersion and a pharmaceutically acceptable carrier.

The pharmaceutically acceptable carrier of the composition according to the present invention includes any conventional diluents, disintegrants, lubricants, and the like. Examples of the diluents include lactose, xylitol, maltitol, cellulose, microcrystalline cellulose, white sugar, silicon dioxide, dextrin, dextrate, calcium dihydrogenphosphate, xanthan gum, polyvinylpyrrolidone, carboxymethyl cellulose, cellulose, glucose, polydextrose, starch, pregelatinized starch, corn starch, Prosolv™, MicroceLac™, hydroxypropyl cellulose, hydroxypropylmethyl cellulose, a mixture thereof, and the like. Examples of the disintegrants include croscarmellose sodium, crospovidone, low-substituted hydroxypropylmethyl cellulose, and the like. Examples of the lubricants include sodium stearyl fumarate, magnesium stearate, calcium stearate, zinc stearic acid, magnesium trisilicate, talc, and the like. The composition according to the present invention further includes additives, such as sodium hydrogencarbonate, sodium starch glycolate, sucrose fatty acid ester, and the like. The kind of the pharmaceutically acceptable carrier can be appropriately selected by one of those skilled in the art, in accordance with a formulation to be obtained.

The pharmaceutical composition may be formulated into various forms, such as a granule, a tablet, a capsule, a dry syrup, or a powder, preferably, a granule, a tablet, or a capsule. Those formulations can be prepared using conventional methods known in the pharmaceutical field. For example, the pharmaceutical composition can be formulated into a tablet by mixing the surface-modified solid dispersion with a diluent, a disintegrant, a lubricant, and the like; and compressing the mixture. Alternatively, the pharmaceutical composition can be formulated into a tablet by granulating a surface-modified solid dispersion with a diluent and the like, mixing the obtained granule with a diluent, a disintegrant, a lubricant and the like, and compressing the obtained mixture. The pharmaceutical composition can be also formulated into a capsule by filling a capsule with the mixture. And also, film-coating or enteric coating can be further performed to improve stability, drug-compliance, and appearance.

The present invention includes, within its scope, a process for preparing the solid dispersion. The process includes: suspending revaprazan and one of a water-soluble polymer, a water-soluble saccharide, a surfactant, and a mixture thereof in water to obtain a suspension; and drying the suspension.

As described above, the use of water as a medium make it possible to avoid potential problems caused by using organic solvents, e.g., safety problems caused by residual solvent.

In the process for preparing the solid dispersion, the suspension can be obtained by adding revaprazan to an aqueous solution containing a water-soluble polymer, a water-soluble saccharide, a surfactant, or a mixture thereof, while strongly stirring the aqueous solution. Alternatively, the suspension can be also obtained by adding both revaprazan and one of a water-soluble polymer, a water-soluble saccharide, a surfactant, and a mixture thereof to water and then strongly stirring the resulting mixture. The stirring (i.e., dispersing) can be performed using any conventional methods known in the pharmaceutical field. For example, the stirring can be performed using a stirrer equipped with a stirring wing, an ultrasonic oscillator, a microfluidizer, a high pressure homogenizer, a propeller-containing mixer, or a homogenizer. Homogeneous suspension can be obtained using a stirrer equipped with a stirring wing and also more homogenous suspension can be obtained using a homogenizer or a microfluidizer.

In the process for preparing the solid dispersion, the drying can be performed using any conventional drying methods known in the pharmaceutical field, such as spray-drying, freeze-drying, or vacuum drying. Preferably, the drying can be performed by spray-drying. The spray-drying can be performed using any conventional methods with a fluid bed granulator or a spray-dryer.

The present invention includes, within its scope, a process for preparing a pharmaceutical composition including the solid dispersion.

For example, according to an embodiment of the present invention, a granule may be prepared by a method which comprises suspending revaprazan and one of a water-soluble polymer, a water-soluble saccharide, a surfactant, and a mixture thereof in water to obtain a suspension; and spray-drying the suspension on a pharmaceutically acceptable carrier. The suspension can be obtained in the same manner as in the method of preparing the solid dispersion.

The spray-drying can be performed according to any conventional methods using a fluid bed granulator, a cylindrical granulator, a high-speed granulator and the like. The pharmaceutically acceptable carrier used in the spray-drying step can include a diluent, such as a microcrystalline cellulose, lactose, corn starch, mannitol, potato starch, pregelatinized starch, cellulose, MicroceLac™, Prosolv™, dextrate, dextrin, calcium dihydrogenphosphate, citric acid, succinic acid, and the like; a disintegrant, such as crospovidone, sodium starch glycolate, croscarmellose sodium, sodium hydrogencarbonate, or low-substituted hydroxypropyl cellulose, and the like; a lubricant, such as magnesium stearate, silicon dioxide, and the like; and a solid surfactant, such as sucrose fatty acid ester (Ryoto Ester™, Mitsubishi Co.), sodium lauryl sulfate, and the like.

Also, according to another embodiment of the present invention, a granule may be prepared by a method which comprises granulating by adding a binder solution to a mixture of the solid dispersion and a pharmaceutically acceptable carrier.

The binder solution may be water; $C_{1-4}$ alcohol (for example, ethanol); a mixture of water and $C_{1-4}$ alcohol (for example, ethanol solution); or a solution prepared by adding any conventional binder used in the pharmaceutical field to one of water, $C_{1-4}$ alcohol (for example, ethanol), and a mixture of water and $C_{1-4}$ alcohol (for example, ethanol solution). The binder includes at least one selected from the group consisting of polyvinyl alcohol, xanthan gum, arabic gum, alginic acid or its salt, polyvinylpyrrolidone, gelatin, hydroxypropylmethyl cellulose, carbomer, hydroxypropyl cellulose, ethyl cellulose and a mixture thereof. The amount of the binder is not limited, and may be about 10 wt % of the total weight of the granulated pharmaceutical composition. When the amount of the binder exceeds 10 wt % of the total weight of the granulated pharmaceutical composition, the granule may be hardened and thus disintegration thereof can be prolonged. When required, the binder solution can further include polyoxyethylene glycolated natural or hydrogenated castor oil (for example, Cremophor RH 40 ™).

Also, according to another embodiment of the present invention, a tablet may be prepared by a method which comprises compressing a mixture of the solid dispersion and a pharmaceutically acceptable carrier, or compressing a mixture of a granule obtained from the solid dispersion and a pharmaceutically acceptable carrier (for example, a lubricant such as magnesium stearate).

Also, according to another embodiment of the present invention, a capsule may be prepared by a method which comprises filling a capsule with a mixture of the solid dispersion and a pharmaceutically acceptable carrier, or filling a capsule with a mixture of a granule obtained from the solid dispersion and a pharmaceutically acceptable carrier The present invention will be described in further detail with reference to the following examples. These examples are for illustrative purposes only and are not intended to limit the scope of the present invention.

EXAMPLE 1

Preparation of Solid Dispersion 20 g of polyvinylpyrrolidone and 80 g of sucrose fatty acid ester (Ryoto Ester L1695™, Mitsubishi Co., Japan) were dissolved in 2,000 ml of purified water. While stirring the resulting solution with a mechanical stirrer, 100 g of revaprazan was added thereto to obtain a suspension. The obtained suspension was spray-dried with Mini spray dryer (Buchi 190) under the condition of: 120 to 130° C. of an inlet temperature and 80 to 90° C. of an outlet temperature to obtain a solid dispersion.

EXAMPLES 2-19

Preparation of Solid Dispersion

Solid dispersions were prepared in the same manner as in Example 1 according to the components and amounts shown in Table 1. The amount of purified water used was 10 ml per 1 g of the total amount of the components used.

TABLE 1

| Ex. | Revaprazan | Polyvinyl-pyrrolidone | Sucrose fatty acid ester | Gelucire 44/14 ™ | Solutol HS 15 ™ | Polysorbate 80 ™ | Cremophor RH 40 ™ | Poloxamer 407 ™ |
|---|---|---|---|---|---|---|---|---|
| 2 | 100 g | | 150 g | | | | | |
| 3 | 100 g | | 100 g | | | | | |
| 4 | 100 g | | 50 g | | | | | |
| 5 | 100 g | | 5 g | | | | | |
| 6 | 100 g | | | | | | | 100 g |
| 7 | 100 g | | | | | | | 50 g |
| 8 | 10 g | | | | | | | 50 g |
| 9 | 100 g | 10 g | 30 g | | | | | |
| 10 | 10 g | | 90 g | | | | | |
| 11 | 100 g | 10 g | 70 g | | | | 15 g | |
| 12 | 100 g | 20 g | 60 g | | 20 g | | | |
| 13 | 100 g | 20 g | 15 g | | | | | 40 g |
| 14 | 100 g | 15 g | 120 g | 20 g | | | | |
| 15 | 100 g | 15 g | | | 11.25 g | | | 26.25 g |
| 16 | 100 g | 20 g | | | | 10 g | 10 g | 50 g |
| 17 | 100 g | 20 g | | | | 15 g | | 60 g |
| 18 | 100 g | 10 g | 60 g | | | | 20 g | 20 g |
| 19 | 10 g | | 50 g | | | 10 g | | 10 g |

EXAMPLE 20

Preparation of Solid Dispersion 20 g of β-cyclodextrin and 80 g of lactose were dissolved in 2,000 ml of purified water. While stirring the resulting solution with a mechanical stirrer, 100 g of revaprazan was added thereto to obtain a suspension. The obtained suspension was homogenized by passing three times through a microfluidizer at a pressure of 10,000-15,000 psi. The obtained suspension was spray-dried with Mini spray dryer (Buchi 190) under the condition of: 120 to 130° C. of an inlet temperature and 80 to 90° C. of an outlet temperature to obtain a solid dispersion.

EXAMPLES 21-32

Preparation of Solid Dispersion

Solid dispersions were prepared in the same manner as in Example 20 according to the components and amounts shown in Table 2. The amount of purified water used was 10 ml per 1 g of the total amount of the components used.

TABLE 2

| Ex. | Revaprazan | Hydroxypropyl β-cyclodextrin | Lactose | Mannitol | Hydroxypropylmethyl cellulose | Vitamin E TPGS ™ | Polyvinyl-pyrrolidone | Polyethylene glycol 6000 | Poloxamer 407 ™ |
|---|---|---|---|---|---|---|---|---|---|
| 21 | 100 g | 100 g | | | | | | 20 g | |
| 22 | 100 g | | 60 g | | | | | | |
| 23 | 100 g | | | 100 g | | | | | |
| 24 | 10 g | 60 g | | 20 g | | | | 20 g | |
| 25 | 100 g | | | | 20 g | 60 g | | | |
| 26 | 100 g | | | | | | 50 g | | |
| 27 | 100 g | | | | 100 g | | | | |
| 28 | 100 g | | | | 50 g | | | 50 g | |
| 29 | 100 g | | 150 g | | | | 50 g | | |
| 30 | 100 g | 10 g | | | 10 g | | | | |
| 31 | 100 g | | 60 g | | | | | | 50 g |
| 32 | 100 g | | 60 g | | 50 g | | | | 50 g |

EXAMPLE 33

Preparation of Solid Dispersion 10 g of polyvinylpyrrolidone, 15 g of Cremophor RH 40™ (produced by BASF Co.), and 70 g of sucrose fatty acid ester (Ryoto Ester™, Mitsubishi Co.) were added to 110 ml of purified water. While stirring the resulting solution with a mechanical stirrer, 100 g of revaprazan was slowly added thereto to obtain a suspension. The obtained suspension was homogenized using a homogenizer at a rotation speed of from 10,000 to 15,000 rpm for ten minutes. The resulting suspension was spray-dried using a fluid bed granulator (produced by Glatt Co.) under the condition of: 110 to 130° C. of an inlet temperature and 1.0 to 2.0 bar of an injection pressure to obtain a surface-modified solid dispersion.

EXAMPLE 34

Preparation of Solid Dispersion-Containing Granules 10 g of polyvinylpyrrolidone, 15 g of Cremophor RH 40™ (produced by BASF Co.), and 50 g of sucrose fatty acid ester (Ryoto Ester™, Mitsubishi Co.) were added to 110 ml of purified water. While stirring the resulting solution with a mechanical stirrer, 100 g of revaprazan was slowly added thereto to obtain a suspension. The resulting suspension was homogenized by stirring at a rotation speed of 300 rpm or more for 2 hours to obtain a homogenized suspension.

67.5 g of microcrystalline cellulose, 20 g of crospovidone, 10 g of sodium hydrogencarbonate, 10 g of sodium starch glycolate, 20 g of sucrose fatty acid ester (Ryoto Ester™, Mitsubishi Co.) were sieved with a 20 mesh-sieve and then mixed together to prepare a carrier for producing a granule.

While the carrier for producing a granule was being fluidized in a fluid bed granulator (produced by Glatt Co.), the above homogenized suspension was spray-dried under the condition of: 50-60° C. of an inlet temperature, 35-45° C. of an outlet temperature and 1.5 bar of an injection pressure to obtain a solid dispersion in a granular form.

EXAMPLES 35-40

Preparation of Solid Dispersion-Containing Granules

Solid dispersions in a granular form were prepared in the same manner as in Example 34 according to the components and amounts shown in Table 3. The amount of purified water used was 1.5 ml per 1 g of the total amount of the components used.

TABLE 3

| | Solid dispersion | | | | | |
|---|---|---|---|---|---|---|
| Ex. | Revaprazan | Polyvinylpyrrolidone | Cremophor RH 40 ™ | Poloxamer 407 ™ | Sucrose fatty acid ester | Vitamin E TPGS |
| 35 | 100 g | 10 g | 15 g | | 70 g | |
| 36 | 100 g | 10 g | 20 g | | 30 g | |
| 37 | 480 g | 48 g | 72 g | | 336 g | |
| 38 | 100 g | | | | 20 g | 10 g |
| 39 | 460 g | | | 57.5 g | | 10.4 g |
| 40 | 100 g | 10 g | 15 g | | 70 g | |

| | Carrier for preparing granules | | | | | | |
|---|---|---|---|---|---|---|---|
| Ex. | Micro crystalline cellulose | Lactose | Corn starch | Crospovidone | Sodium hydrogencarbonate | Sodium starch glycolate | Sucrose fatty acid ester |
| 35 | 30 g | 37.5 g | | 20 g | 10 g | 10 g | |
| 36 | 70 g | | | 20 g | 10 g | 10 g | 40 g |
| 37 | 324 g | | | 48 g | 48 g | | |
| 38 | | 70 g | 20 g | 5 g | | | |
| 39 | 225 g | 188 g | | 25 g | 25 g | | |
| 40 | 150 g | | | | | | |

EXAMPLE 41

Preparation of Solid Dispersion-Containing Granules

A mixture of 481.5 g of microcrystalline cellulose, 360 g of sucrose fatty acid ester (Ryoto Ester™, Mitsubishi Co.), 90 g of crospovidone, and 90 g of sodium hydrogencarbonate was sieved with a 20 mesh-sieve, and then 1,260 g of the solid dispersion prepared according to Example 9 was added thereto. The resultant mixture was mixed in a high-speed granulator for 1 minute. A binder solution was prepared by dissolving 135 g of Cremophor RH 40™ in 90 ml of 50% (v/v) ethanol solution. While rotating the mixture in the high-speed granulator at a speed of 300 rpm for 3 minutes, the binder solution was added thereto to obtain the solid dispersion-containing granules.

EXAMPLES 42-44

Preparation of Solid Dispersion-Containing Granules

Solid dispersion-containing granules were prepared in the same manner as in Example 41 according to the components and amounts shown in Table 4.

TABLE 4

|  | Example 42 | Example 43 | Example 44 |
|---|---|---|---|
| Solid dispersion of Example 1 | 1,200 g | | |
| Solid dispersion of Example 5 | | 1,260 g | |
| Solid dispersion of Example 11 | | | 1,170 g |
| Microcrystalline cellulose | 700 g | | 700 g |
| Lactose | | | 200 g |
| Crospovidone | 100 g | | 100 g |
| Sodium hydrogencarbonate | 100 g | | 100 g |
| Sucrose fatty acid ester | | 300 g | |
| Cremophor RH 40 ™ | 300 g | 300 g | 100 g |

EXAMPLES 45-48

Surface-Modified Solid Dispersion-Containing Granule

According to the components and amounts shown in Table 5, solid dispersion-containing granules were prepared in the same manner as in Example 41, except that Cremophor RH 40™ was not used and 90 ml of 50% (v/v) ethanol solution was used as a binder solution.

TABLE 5

|  | Example 45 | Example 46 | Example 47 | Example 48 |
|---|---|---|---|---|
| Solid dispersion of Example 3 | 1,200 g | | | |
| Solid dispersion of Example 6 | | 1,200 g | | |
| Solid dispersion of Example 14 | | | 1,530 g | |
| Solid dispersion of Example 17 | | | | 1,170 g |
| Microcrystalline cellulose | 500 g | 500 g | 700 g | 700 g |
| Lactose | 300 g | | | |
| Corn starch | | 300 g | 200 g | |
| Crospovidone | 90 g | 100 g | 100 g | 100 g |
| Sodium hydrogencarbonate | 90 g | 100 g | | |
| Sodium starch glycolate | | | 100 g | 100 g |
| Sucrose fatty acid ester | 200 g | | | |

EXAMPLE 49

Preparation of Solid Dispersion-Containing Granule

A mixture of 500 g of microcrystalline cellulose, 360 g of sucrose-fatty acid ester (Ryoto Ester™, Mitsubishi Co.), 90 g of crospovidone, and 90 g of sodium hydrogencarbonate was sieved with a 20 mesh-sieve, and then 1,300 g of the solid dispersion prepared according to Example 9 was added thereto. The resultant mixture was mixed in a high-speed granulator for 1 minute. A binder solution was prepared by dissolving 20 g of hydroxypropylmethyl cellulose in 100 ml of 80% (v/v) ethanol solution. While rotating the mixture in the high-speed granulator at a speed of 300 rpm for 3 minutes, the binder solution was added thereto to obtain the solid dispersion-containing granules.

EXAMPLE 50

Preparation of Tablet 200 g of the solid dispersion prepared according to Example 1, 150 g of microcrystalline cellulose, 20 g of sodium starch glycolate, 20 g of crospovidone, and 10 g of magnesium stearate were mixed and then compressed using a single tablet press to obtain tablets (Weight per tablet: 800 mg and Amount of revaprazan per tablet: 200 mg).

EXPERIMENTAL EXAMPLE 1

Dissolution Test

Solubility of a revaprazan-containing solid dispersion was measured in purified water. A solid dispersion containing 1 g of revaprazan was added to a beaker containing 50 ml of purified water, which was then strongly stirred using a magnetic stirrer at 25° C. in a water bath for 6 hours. After 1, 2, and 6 hours, each sample was collected and filtered using a 0.45 µm filter. The filtrate was diluted with methanol having such an amount that absorbance of the filtrate is in the range from 0.2 to 1.0. Then, absorbance of the diluted filtrate was measured at 270 nm using a UV spectrophotometer (Agilent 8453, Agilent technologies, USA). From the obtained absorbance value, concentrations of revaprazan were obtained using a standard curve.

About 20 mg of revaprazan standard was dissolved in methanol until the total volume of the solution reached 10 ml. 1 ml of the resultant solution was added to a 100 ml flask and then purified water was added thereto to obtain a standard stock solution. The standard stock solution was diluted with purified water to obtain 2 µg/ml, 5 µg/ml, 8 µg/ml, and 10

µg/ml of standard solution. Each absorbance of the standard solutions was measured at an absorption maximum wavelength of 270 nm to obtain a standard curve. The standard curve was moderately linear passing through almost (0.0) (coefficient of correlation $r^2$>0.98). The results are shown in Table 6.

TABLE 6

|  | Solubility (ug/ml) |
| --- | --- |
| Revaprazan powder | 173 |
| Example 2 | 905 |
| Example 3 | 505 |
| Example 4 | 237 |
| Example 6 | 303 |
| Example 7 | 240 |
| Example 18 | 803 |

Referring to Table 6, it can be seen that solubility of the surface-modified solid dispersion according to the present invention is remarkably improved.

EXPERIMENTAL EXAMPLE 2

Adhesiveness and Agglutination Test

The bulk density and tapped density of revaprazan powder and the surface-modified solid dispersions prepared according to Examples 3 and 6 were measured and their Carr's indexes were obtained in order to measure flowability thereof. About 3 g of a solid dispersion was carefully added to a plastic measuring cylinder and the volume thereof was measured to obtain the bulk density. And then, this was subjected to tapping 3,000 times using a tapped density meter to measure the volume and the tapped density was obtained. From the obtained bulk density and tapped density, Carr's index was calculated in order to evaluate flowability. The results are shown in Table 7.

TABLE 7

|  | Carr's index |
| --- | --- |
| Revaprazan powder | 41.2 |
| Example 3 | 21.9 |
| Example 6 | 17.6 |

ρo: Bulk density
ρt: Tapped density
Carr's index = (ρo − ρt)/ρt * 100

Referring to Table 7, revaprazan powder having very high adhesion and agglutination properties shows 40% or more of Carr's index and its flowability was very low. On the other hand, the surface-modified solid dispersion had high flowability and its compression properties were improved.

EXPERIMENTAL EXAMPLE 3

Observation of Particle Surface Using Scanning Electron Microscope

The surface of particles of a revaprazan-containing solid dispersion was measured using a scanning electron microscope (SEM). The samples prepared according to Examples 6 and 11 were mounted on a metal stub to which a double-sided tape had been attached, and then coated with platinum using an ion sputtering device (JFC-1100E, Jeol Co., Japan) in argon gas atmosphere. Each of the coated samples was loaded to SEM (JSM 5410LV, JEOL Co., Japan). The magnification was adjusted at a voltage of 15 kV to observe the surface of particles. As a reference, the shape of revaprazan particles was also observed using a polarizing microscope to compare with those of the surface-modified solid dispersions described above. Revaprazan was placed on a slide glass and then a few drops of mineral oil were dropped thereto for dispersing. The sample was covered with a cover glass and then loaded on a mobile plate of a polarizing microscope (Nikon eklipse E600 POL, Nikon Co., Japan) to observe the shape of the crystal while a polarization angle was being adjusted.

Figure 3:
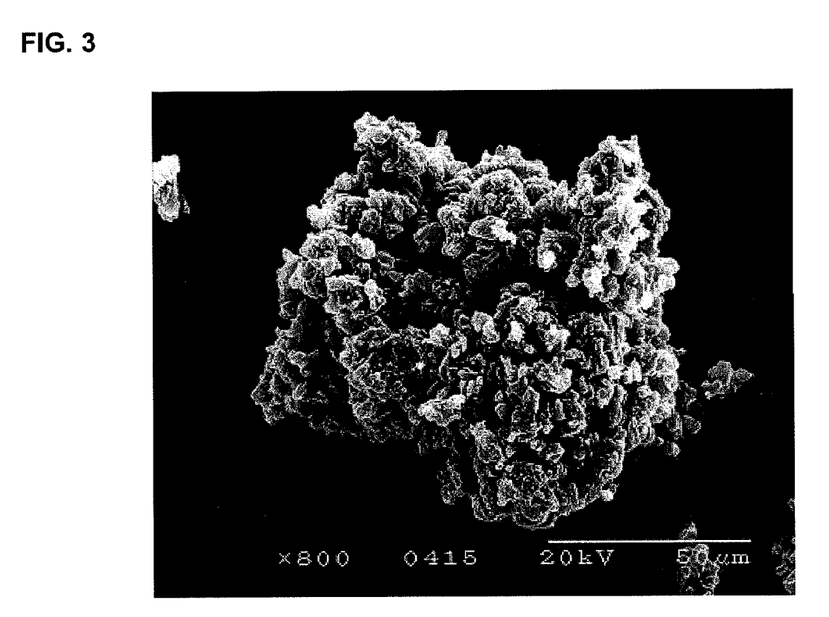
FIG. 3 is a scanning electron microscopic image of a solid dispersion (Example 6) prepared according to the present invention.
Figure 4:
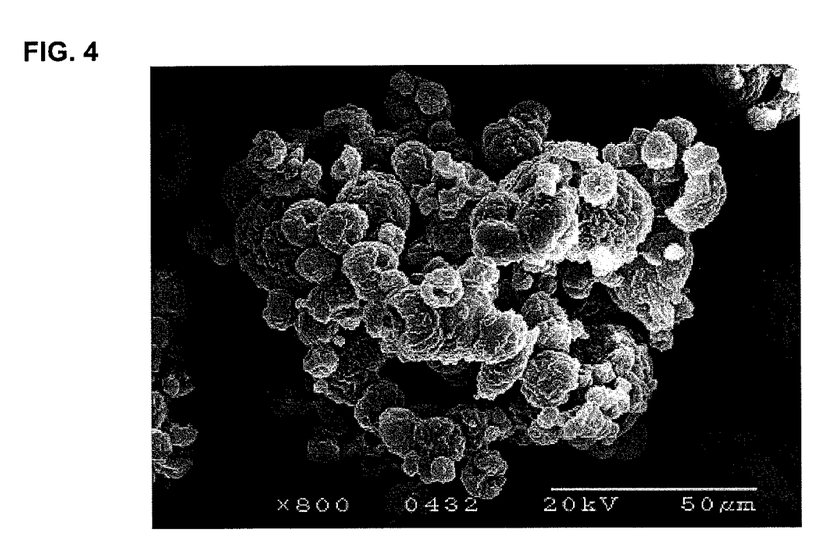
FIG. 4 is a scanning electron microscopic image of a solid dispersion (Example 11) prepared according to the present invention.
Figure 5:
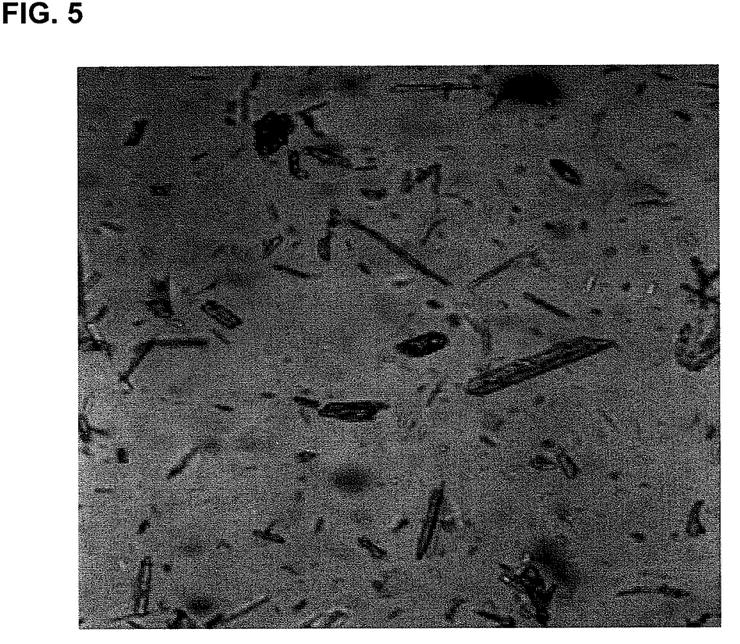
FIG. 5 is a polarizing microscopic image of revaprazan particles.

Referring to FIGS. 3 and 4, revaprazan does not show any crystalline image. However, the revaprazan-containing solid dispersions show crystalline forms covered with surface-modifying materials.

EXPERIMENTAL EXAMPLE 4

Comparative Dissolution Test

Comparative dissolution test was performed to evaluate dissolution profile of a surface-modified solid dispersion according to the present invention. A revaprazan-containing capsule was prepared as a comparative sample. Specifically, 50 mg of revaprazan powder was mixed with 10% (w/w) of sodium starch glycolate as a disintegrant. The mixture was filled into a hard gelatin capsule. The solid dispersion prepared according to Example 3 was mixed with 10% (w/w) of sodium starch glycolate and then the resulting mixture was filled into a hard gelatin capsule. A dissolution test was performed on the tablet prepared according to Example 36 and the above samples in 900 ml of 0.1 N HCl solution at 37±0.5° C. of temperature and 50 rpm of an agitation speed. 3 ml of the sample was collected in every 15 minutes, 30 minutes, 45 minutes, 60 minutes, and 90 minutes and the same amount of the medium was compensated immediately. From the collected dissolution sample, the dissolution rate was measured by quantifying the concentration of revaprazan at 270 nm using UV spectrometer. The results are shown in FIG. 1.

Figure 1:
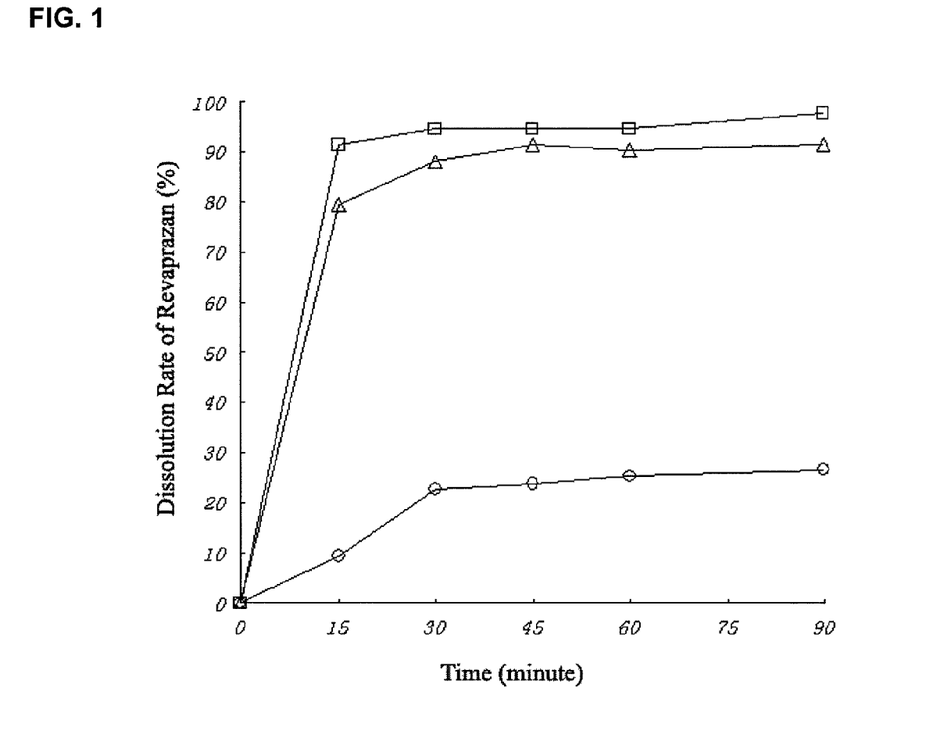
FIG. 1 shows results of the comparative dissolution test of formulations prepared according to the present invention and a conventional formulation [a capsule containing the solid dispersion prepared according to Example 3 (△), a tablet prepared according to Example 3 (□), and a capsule filled with revaprazan powder (○)].
Figure 2:
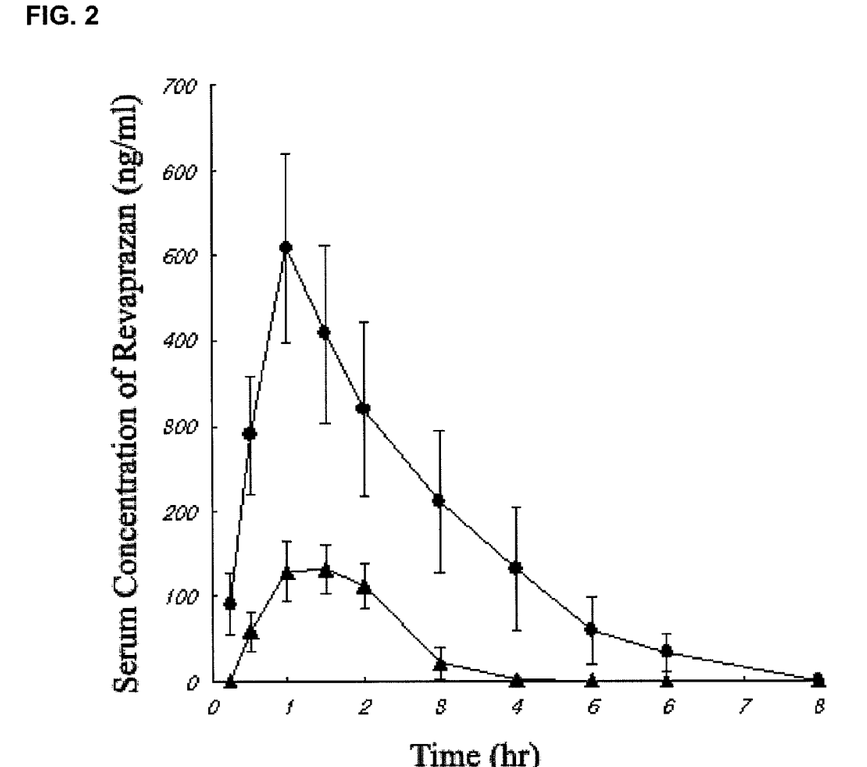
FIG. 2 shows results of pharmacokinetic studies using a beagle dog of a formulation prepared according to the present invention and a conventional formulation [a tablet prepared according to Example 36 (●) and a capsule filled with revaprazan powder (▲)].

Referring to FIG. 1, the revaprazan powder formulation has 30% or less of dissolution rate, but the formulations according to the present invention have as high dissolution rate as 95% or more within 30 minutes.

EXPERIMENTAL EXAMPLE 5

Pharmacokinetic Study

About 10 kg of male beagle dogs were chosen, their weight was measured, and they were confirmed with naked eyes whether or not they had any wound. Before administration of the test materials, any food was not provided to the beagle dogs except for water for 15 hours. Then, a revaprazan tablet (comparative formulation) prepared from a mixture of revaprazan, lactose, sodium starch glycolate, and magnesium stearate, and the table prepared according to Example 36 were orally administered with 20 to 40 ml of water. The administrated dosage was 200 mg of revaprazan per subject. Before the administration, and 0.25, 0.5, 1, 1.5, 2, 3, 4, 6, and 8 hours after the administration, about 1.0 ml of blood was collected using a heparin-treated injector. The collected blood was centrifuged at a rotation speed of 3,000 rpm for 5 minutes, and the separated serum was loaded to an effendorf tube and left to sit at −20° C. Then, the frozen collected blood was defrosted and then the amount of revaprazan in serum was measured using HPLC.

The maximum serum concentration (Cmax) and the time required to reach the maximum serum concentration (Tmax) were measured using values obtained from the serum concentration-time curve, and the area under the serum concentration-time curve from 0 hour to 8 hours ($AUC_{0-8hr}$) was measured using a trapezoidal rule. $AUC_{0-\infty}$, the area under the serum concentration-time curve from 0 hours to $\infty$, was measured using a trapezoidal rule extrapolation. The area under the serum concentration-time curve from the final data to $\infty$ was obtained by dividing the final serum concentration by the elimination constant. The blood concentration of the drug and pharmacokinetic parameters were represented by mean±S.E.M. values, and a statistical significance of in vivo experiment results was calibrated using Duncun's multiple range test according to analysis of variance.

$AUC_{0-8hr}$(ng·hr/ml) of the tablet prepared according to Example 36 was 1401±332, five-fold higher than $AUC_{0-8hr}$ (ng·hr/ml), i.e, 261±52, of a conventional revaprazan tablet (p<0.05). As for Cmax obtained from blood concentration-time curve, Example 36 had 652 ng/ml, and a conventional revaprazan tablet had 165 ng/ml.

The invention claimed is:

1. A solid dispersion comprising particles of revaprazan, wherein the revaprazan particles are in a crystalline form and are surface-modified with a water-soluble polymer, a water-soluble saccharide, a surfactant, or a mixture thereof,
    wherein the water-soluble polymer is selected from the group consisting of polyvinylpyrrolidone, hydroxypropylmethyl cellulose, hydroxypropyl cellulose, polyethylene glycol, a water-soluble polyacrylic acid copolymer, polyvinyl alcohol, and a mixture thereof;
    wherein the water-soluble saccharide is selected from the group consisting of lactose, white sugar, sucrose, mannitol, sorbitol, xylitol, trehalose, maltitol, dulcitol, inositol, dextrin, cyclodextrin, and a mixture thereof; and
    wherein the surfactant is selected from the group consisting of sorbitan ester or polyoxyethylene sorbitan fatty acid ester, sucrose fatty acid ester, polyethylene glycol-15-hydroxystearate, polyoxyethylene glycolated natural or hydrogenated castor oil, polyoxyethylene-polyoxypropylene copolymer, synthetic vitamin E derivative, polyoxyethylene alkyl ester, fatty acid microgol glyceride, polyglyceryl fatty acid ester, bile acid, sodium lauryl sulfate, lecithin, glyceryl fatty acid ester, polyoxyethylene stearate, and a mixture thereof.

2. The solid dispersion of claim 1, wherein the revaprazan particles are surface-modified with polyvinylpyrrolidone, sucrose fatty acid ester, and polyoxyethylene glycolated natural or hydrogenated castor oil.

3. The solid dispersion of claim 1, wherein the revaprazan particles are surface-modified with one of a water-soluble polymer, a water-soluble saccharide, a surfactant, and a mixture thereof in an amount from 5 to 900 parts by weight, based on 100 parts by weight of revaprazan.

4. The solid dispersion of claim 3, wherein the revaprazan particles are surface-modified with one of a water-soluble polymer, a water-soluble saccharide, a surfactant, and a mixture thereof in an amount from 20 to 200 parts by weight, based on 100 parts by weight of revaprazan.

5. The solid dispersion of claim 1, wherein the revaprazan particles are surface-modified with 5 to 30 parts by weight of polyvinylpyrrolidone, 20 to 100 parts by weight of sucrose fatty acid ester, and 10 to 100 parts by weight of polyoxyethylene glycolated natural or hydrogenated castor oil, based on 100 parts by weight of revaprazan.

6. A pharmaceutical composition comprising the solid dispersion according to claim 1 and a pharmaceutically acceptable carrier.

7. The pharmaceutical composition of claim 6, wherein the pharmaceutical composition is in the form of a granule, a tablet, a capsule, a dry syrup, or power.

* * * * *